(12) United States Patent
Giannessi et al.

(10) Patent No.: US 6,822,115 B2
(45) Date of Patent: Nov. 23, 2004

(54) SYNTHESIS OF (R) AND (S)-AMINOCARNITINE, (R) AND (S)-4-PHOSPHONIUM-3-AMINO-BUTANOATE, (R) AND (S) 3,4-DIAMINOBUTANOIC ACID, AND THEIR DERIVATIVES STARTING FROM D- AND L-ASPARTIC ACID

(75) Inventors: Fabio Giannessi, Pomezia (IT); Natalina Dell'uomo, Pomezia (IT); Maria Ornella Tinti, Rome (IT); Francesco De Angelis, Rome (IT)

(73) Assignee: Sigma-Tau Industrie Farmaceutiche Riunite S.p.A., Rome (IT)

( * ) Notice: Subject to any disclaimer, the term of this patent is extended or adjusted under 35 U.S.C. 154(b) by 0 days.

(21) Appl. No.: 10/372,627

(22) Filed: Feb. 25, 2003

(65) Prior Publication Data

US 2003/0153784 A1 Aug. 14, 2003

Related U.S. Application Data

(63) Continuation-in-part of application No. 10/338,045, filed on Jan. 8, 2003, now abandoned, which is a continuation-in-part of application No. 10/018,794, filed as application No. PCT/IT00/00258 on Jun. 23, 2000, now Pat. No. 6,528,624.

(30) Foreign Application Priority Data

Jun. 30, 1999 (IT) ........................... RM99A0418

(51) Int. Cl.[7] ............................................. C07C 229/00
(52) U.S. Cl. ........................... 562/561; 562/567
(58) Field of Search ........................... 562/567, 561, 562/556

(56) References Cited

U.S. PATENT DOCUMENTS 4,413,142 A   11/1983   Fiorini et al.
6,528,684 B1   3/2003   Giannessi et al.

FOREIGN PATENT DOCUMENTS

EP   0 636 603 A   2/1995

OTHER PUBLICATIONS

Charles W. Jefford et al.; "The Enantioselective Synthesis of Beta-Amino Acids, Their Alpha-Hydroxy Derivatives and the N-Terminal Components of Bestatin and Microginin"; Helvetica Chimica Acta, vol. 79, 1996; pp. 1203–1216; XP002152295.

*Primary Examiner*—Paul A. Zucker
(74) *Attorney, Agent, or Firm*—Nixon & Vanderhye P.C.

(57) ABSTRACT

R or S aminocarnitine, R or S phosphonium aminocarnitine and R and S 3,4 diaminobutanoic acid, and their derivatives are prepared using

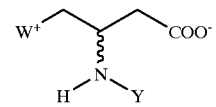

starting from aspartic acid with the same configuration as the desired compounds. This process is advantageous from the industrial point of view in terms of the type of reactants used, the reduced volumes of solvents and the possibility of avoiding purification of the intermediate products.

15 Claims, No Drawings

SYNTHESIS OF (R) AND (S)-AMINOCARNITINE, (R) AND (S)-4-PHOSPHONIUM-3-AMINO-BUTANOATE, (R) AND (S) 3,4-DIAMINOBUTANOIC ACID, AND THEIR DERIVATIVES STARTING FROM D- AND L-ASPARTIC ACID

This application is a continuation-in-part of application Ser. No. 10/338,045 filed Jan. 8, 2003, abandoned, which is a continuation-in-part of Ser. No. 10/018,794 filed Dec. 21, 2001, now U.S. Pat. No. 6,528,684 which is a 35 USC §371 of PCT/IT00/00258 filed Jun. 23, 2000.

The invention described herein relates to a process for the production of (R) and (S)-aminocarnitine and its derivatives starting from D- and L-aspartic acid. The same process can be applied to produce other related compounds such as (R) and (S)-4-phosponium-3-amino-butanoate and its derivatives or (R) and (S) 3,4-diamino butanoic acid dihydrochloride.

Aminocarnitine is a substance endowed with interesting pharmaceutical properties and its N-derivatives arouse a similar degree of interest. For example, D. L. Jenkins and W. O. Griffith have described the antiketogenic and hypoglycaemic effects of the N-acetylates in the racemic form. U.S. Pat. No. 4,521,432 (Takeda) describes the possible applications of (−)-N-acetyl-aminocarnitine, inner salt, in the treatment of the complications of diabetes. Similar activity has been described for (+)-aminocarnitine, chloride hydrochloride. It would therefore be of interest to have processes for the preparations of the enantiomorph, which match up to the criteria of economic convenience on an industrial scale.

R(+)-aminocarnitine is obtained via hydrolysis of R-(−)-N-acetylcarnitine, the latter being isolated by the cultivation of micro-organisms of the genera *Emericella* or *Aspergillus*, or, alternatively, via a complex chemical process described in the Takeda patent cited above.

Other methods of chemical synthesis are known, all rather complex, such as, for example, the one described by Shinagawa, J. Med. Chem., 30; 1458 (1987), who uses diazomethane, which is known to be hazardous. In any event, this method is not of industrial interest, in that it was conceived in order to ascertain the absolute configuration of the single enantiomorph.

The single enantiomorphs can also be obtained by resolution of the racemic mixture of (±)-N-acetylaminocarnitine, as described in EP 0 287 523.

Alternatively, R(+)- and S(−)-aminocarnitine chloride can be obtained by resolution on silica gel chromatography or fractional crystallisation of the respective N-α-methylbenzyl, benzylester chlorides, as described in Italian patent 1,231,751. This process, which involves subsequent debenzylation is laborious and not very suitable for industrial-scale production.

A method is also known using chiral carnitine as a starting product (*Journal of Organic Chemistry*, 1995, 60, 8318–8319; (Sigma-Tau) EP 636603, 1995). This method uses reagents such as methane-sulphonic anhydride and sodium azide and solvents such as anhydrous dimethylsulphoxide, and involves a catalytic reduction step.

A process has now been found for the preparation of single enantiomorphs starting from D-aspartic acid and L-aspartic acid, respectively, with an overall yield of at least 38% in 6 to 7 steps, but without it being necessary to purify the intermediates. In pratice, the process according to the invention described herein is realised via direct hydrolysis of the chiral aminocarnitine ester in an acidic milieu to yield a chiral aminocarnitine inner salt without purifying the intermediate products. The enantiomeric purity of the aminocarnitine thus obtained is >99%.

The same synthetic process can be performed to prepare new compounds such as (R) and (S) 4-phosphonium-3-aminobutanoate (hereinafter referred as phosphonium aminocarnitine) and a chiral synthon as (R) and (S) 3,4-diaminobutanoic acid dihydrochloride.

4-phosphonium-3-aminobutanoate is potentially useful as CPT inhibitor with antiketogenic and hypoglycemic effects and as intemediate for the synthesis of pharmacologically active compounds.

Thus, an object of the invention described herein is a process for the preparation of (R) and (S)-aminocarnitine, (R) and (S) phosphonium aminocarnitine and of a number of their N-substituted derivatives, and a process for the preparation of (R) and (S) 3,4-diaminobutanoic acid dihydrochloride (*Synlett* 1990, 543–544; *Synth. Comm.* 1992, 22(6), 883–891). In particular, the invention described herein provides a process which also enables aminocarnitine, phosphonium aminocarnitine and 3,4-diaminobutanoic acid derivatives to be obtained which are useful for the preparation of medicaments for the treatment of diseases associated with hyperactivity of carnitine palmitoyltransferase.

These derivatives are described in Italian patent application MI98A001075, filed on 15 May 1998, and in international patent application PCT/IT99/00126, filed on 11 May 1999, both of which in the name of the applicant and incorporated herein for reference purposes.

The process according to the invention described herein allows the preparation of compounds with the following formula:

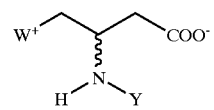

in which
W is $Q(CH_3)_3$ where Q is N or P
or
W is $NH_3$
Y is hydrogen or one of the following groups:
—$R_1$,
—$COR_1$,
—$CSR_1$,
—$COOR_1$,
—$CSOR_1$,
—$CONHR_1$,
—$CSNHR_1$,
—$SOR_1$,
—$SO_2R_1$,
—$SONHR_1$,
—$SO_2NHR_1$,
where
$R_1$ is a straight or branched, saturated or unsaturated alkyl containing from 1 to 20 carbon atoms, optionally substituted with an $A_1$ group, where $A_1$ is selected from the group consisting of halogen, $C_6$–$C_{14}$ aryl or heteroaryl, aryloxy or heteroaryloxy, which can optionally be substituted with straight or branched, saturated or unsaturated lower alkyl or alkoxy, containing from 1 to 20 carbon atoms, halogens;

said process comprises the following steps:
a) conversion of D-aspartic or L-aspartic acid to N—Y substituted D-aspartic or L-aspartic acid;
b) conversion of the N—Y substituted D-aspartic or L-aspartic acid to the respective anhydride;
c) reduction of the anhydride obtained in step b) to the corresponding 3-(NH—Y)-lactone;
d) opening of the lactone obtained in step c) to yield the corresponding D- or L-3-(NH—Y)-amino-4-hydroxybutyric acid;
e) transformation of the 4-hydroxy group of the D- or L-3-(NH—Y)-amino-4-hydroxybutyric acid into a leaving group;
f) substitution of the end group in position 4 of the D- or L-3-(NH—Y)-aminobutyric acid with a trimethylammonium group or with a trimethylphosphonium group
g) hydrolysis of the ester group; and, if so desired,
h) restoration of the amino group.

The usefulness of this new synthesis route for optically pure aminocarnitine, as compared to the method involving the use of chiral carnitine as the starting product (*Journal of Organic Chemistry*, 1995, 60, 8318–8319; EP 0 636 603 (Sigma-Tau)), consists in the fact that the use of reactants such as methane-sulphonic anhydride and sodium azide, of dimethyl-sulphoxide as a solvent, and of a catalytic reduction step is avoided. What is more, the volumes involved are lower, thus allowing better management of the reactions and of any purification of intermediate products. In fact, the process according to the invention presents the additional advantage that all steps can be carried out avoiding purification of the intermediates, without this jeopardising the purity of the end product. This advantageous characteristic is obvious to the expert in the art; in particular, the fact will be appreciated that that no purification operations are necessary which would place an additional burden on the synthesis process in terms of economic costs, time, materials, specialised personnel and equipment.

As compared to the process described in *Journal of Medicinal Chemistry*, 1987, 30, 1458–1463 (Takeda), involving the use of benzyloxycarbonyl-L-asparagine as the starting product (with 7 steps and a 24% overall yield), the advantage at industrial level of avoiding reactants such as diazomethane, silver benzoate and dimethyl-sulphate appears obvious. In another process (*Bioorganic & Medicinal Chemistry Letters*, 1992, 2 (9), 1029–1032), (R)-aminocarnitine is obtained starting from a derivative of aspartic acid (the tert-butylester of N-benzyloxycarbonyl-L-aspartic acid) in seven steps with a yield of 24% 22%, but again using reactants such as diazomethane and silver benzoate, a catalytic hydrogenation step, and methylation with methyl iodide.

In these previously mentioned syntheses, the only product that can be obtained is (R)-aminocarnitine. The great versatility of this new route allows instead to obtain several compounds such as (R)-phosphonium aminocarnitine and (R) 3,4-diaminobutanoic acid dihydrochloride, just changing the incoming nucleophile.

The processes which are the subject of the invention described herein are described in the scheme, for (R)-forms. It is absolutely obvious to the expert in the sector that the case of S-(−)-forms is equally described by the scheme and that no modification is necessary, apart from the fact that the starting compound is of the opposite configuration, namely S-(−)-aspartic acid.

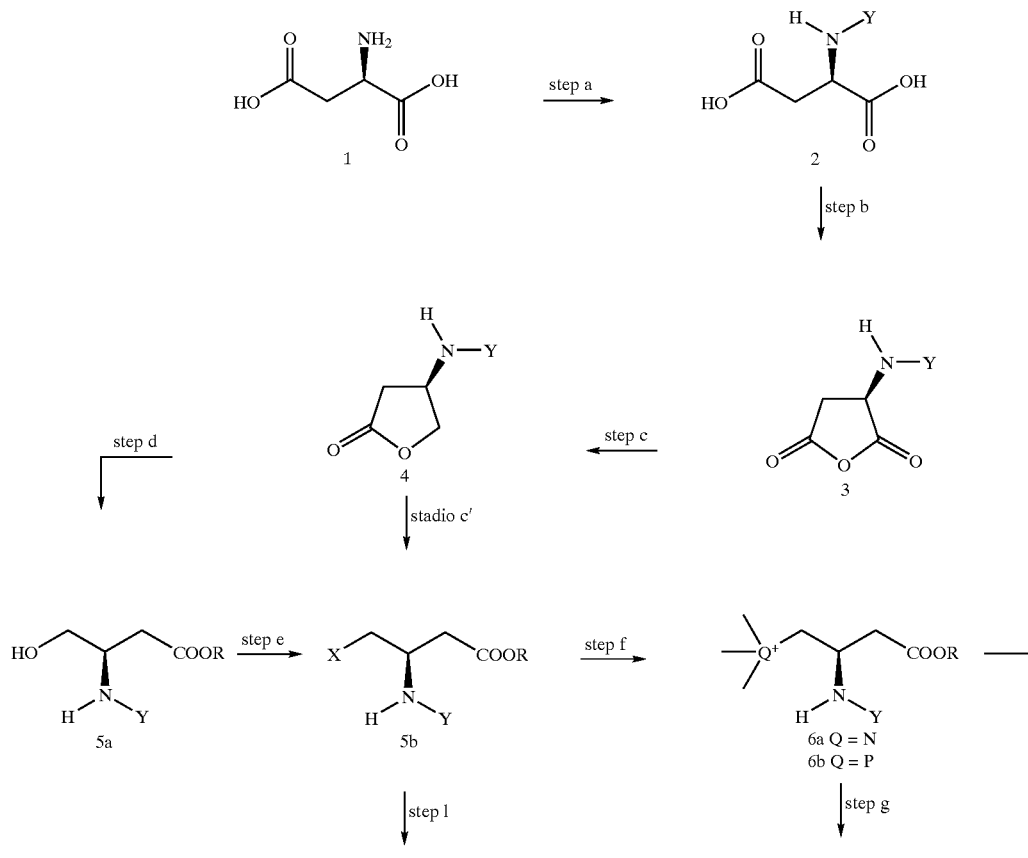

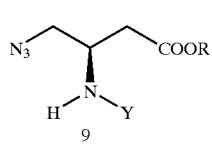

9

↓ step m

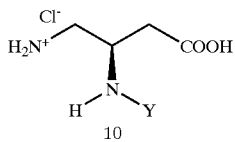

10

↓ step n

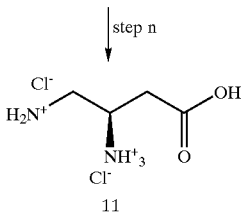

11

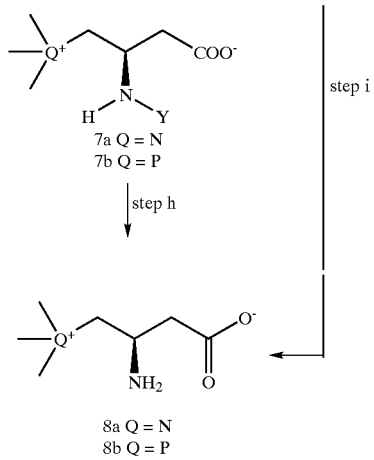

7a Q = N
7b Q = P

↓ step h

8a Q = N
8b Q = P step i

In the context of the invention described herein, examples of the straight or branched $C_1$–$C_{20}$ alkyl group are methyl, ethyl, propyl, butyl, pentyl, octyl, nonyl, decyl, undecyl, dodecyl, tridecyl, tetradecyl, pentadecyl, hexadecyl, heptadecyl, octadecyl, nonadecyl and eicosyl and their possible isomers, such as, for example, isopropyl, isobutyl and tert-butyl.

Examples of the ($C_6$–$C_{14}$) aryl, or ($C_6$–$C_{14}$) aryloxy, heteroaryl or heteroaryloxy group, possibly substituted with straight of branched alkyl or alkoxy with from 1 to 20 carbon atoms, said alkyl group being as exemplified above, are phenyl, 1- or 2-naphthyl, anthracenyl, benzyl, 2-phenylethyl 1-phenylethyl, 3-phenylpropyl, 2-anthracenylpropyl, 1-anthracenylpropyl, naphthylmethyl, 2-naphthylethyl, 1-naphthylethyl, 3-naphthylpropyl, 2-naphthyl-propyl, 1-naphthylpropyl, cyclohexylmethyl, 5-phenylpentyl, 3-phenylpentyl, 2-phenyl-3-methylbutyl, thienyl, quinolyl, pyridyl, 5-tetrazolyl, and the equivalent ether derivatives.

What is meant by halogen is fluorine, chlorine, bromine, or iodine.

In a first embodiment of the invention described herein, the process involves steps a)–g), and optionally h), described above. According to this first realisation, and with reference to the scheme given above, commercial chiral aspartic acid 1 is treated with a reactant suitable for introducing the Y group on the nitrogen atom. This step both functions to protect the amino group in the subsequent steps of the process and, if suitably selected, represents the group which will be present in the end compound, according to the meanings attributed above to the Y group.

Assuming that, in the end compound, the Y group is other than hydrogen, different cases may be envisaged in the process according to the invention.

In the case in which Y is $R_1$, the substitution reaction of a hydrogen of the amino group takes place by reaction with alkancarbaldehydes, where the alkyl portion is a homologue of an lower term of the $R_1$ group desired, and subsequent reduction.

When Y is —$COR_1$, —$CSR_1$, —$COOR_1$, —$CSOR_1$, —$CONHR_1$, —$CSNHR_1$, —$SOR_1$, —$SO_2R_1$, —$SONHR_1$ and —$SO_2NHR_1$, the compounds are obtained by reaction with acylic chlorides, thioacylic chlorides, alkyl chloroformates, alkyl thiochloroformates, alkyl isocyanates, alkyl thioisocyanates, alkly sulphinyl chlorides, alkyl sulphonyl chlorides, $SOCl_2$ and alkyl amines, alkyl sulphamoyl chlorides (or $SO_2Cl_2$ and alkyl amines), containing the desired alkyl $R_1$ group.

As regards the different meanings of $R_1$, present in the various reactants, these are available commercially, or can be prepared according to known methods described in the literature, to which the expert in the art may refer, completing his general knowledge of the subject.

In a second embodiment of the invention described herein, the process involves steps a)–c), and then a step c'), that is to say the opening of the lactone with the introduction of a leaving group X, followed by step l) or by steps f) and g) and optionally h), described above.

In a third embodiment of the invention described herein, the process requires that step f), which has been reached according to one of the first two embodiments of the invention, be followed by step i), i.e. the direct transformation of the ester of the N—Y substituted aminocarnitines to aminocarnitines. In a fourth embodiment of the invention described herein the leaving group X, introduced as described above, has been substituted with an azido group in step l), the resulting azido derivative has been subjected to catalitic reduction in step m), optionally followed by the hydrolis of Y performed in step n).

In a preferred form, and by way of an example, commercial chiral aspartic acid 1 is protected to yield derivative 2. Protective groups (Y in the scheme) are well known and require no particular description. As an example, we may cite the tosyl group, which, in the reaction envisaged in the invention, is described in *Helv. Chim. Acta* 1996, 79, 1203–1216, or the benzyloxycarbonyl group, which, in the reaction envisaged in the invention, is described in *J. Am.*

*Chem. Soc.* 1986, 108, 4943–4952. Thus, derivative 2 is cyclised to anhydride 3, as described, for example, in *Helv. Chim. Acta* 1994, 77, 2142–2146, and subsequently reduced to lactone 4 (see *Helv. Chim. Acta* 1994, 77, 2142–2146).

Compound 4 can be transformed into compound 5a by treatment with an alcohol ROH, where R is a straight or branched 1 to 14 term alkyl, or an arylalkyl, e.g. methanol, isobutanol or benzyl alcohol, in the presence of a suitable transesterification catalyst, such as, for example, an acid or a base (also in the form of resin), preferably amine, such as trimethylamine. By treatment with a reactant suitable for transforming the hydroxyl into an end group, e.g. alkyl or arylsulphonyl chlorides, such as methane sulphonyl chloride in pyridine, triflic anhydride, 5a yields 5b, which by reaction with trimethylamine or trimethyl phosphine yields 6a or 6b. Aminocarnitine or phosphonium aminocarnitine can be obtained respectively from 6a and 6b by hydrolysing the ester and deprotecting the amino group according to customary procedures.

In accordance with the second embodiment of the process according to the invention, step c') involves the opening of the lactone with iodotrimethylsilane, described in the literature when ethanol is used as the alcohol (*Helv. Chim. Acta*, 79, 1996, 1203–1216) and makes it possible to obtain the iododerivative 5b (X=iodine) with good yields. Similar lactone opening reactions can, of course, be easily envisaged with other leaving groups.

Thus, intermediate 5b is treated in a nucleophilic substitution reaction with trimethylamine or trimethylphosphine to yield intermediates 6a or 6b, which, by alkaline hydrolysis and subsequent deprotection of the amine group supply the desired products, e.g. on deprotecting with 48% HBr, dibromohydrate is obtained. After a step on IRA 402 resin (OH$^-$) aminocarnitine inner salt 8a or phosphonium aminocarnitine inner salt 8b are obtained.

According to the third embodiment of the invention described herein, on proceeding directly to the acid hydrolysis of 6a or 6b to give 8a or 8b the overall yield rises to 38% or 36% respectively in six steps. The enantiomeric purity of the aminocarnitine and of phosphonium aminocarnitine thus obtained (determined by means of conversion to the derivative obtained with o-phthalaldehyde and L-acetylcysteine and HPLC analysis, see *J. Chromatography*, 1987, 387, 255–265) was >99%.

In accordande with the fourth embodiment of the process according to the invention, step l) provides the nucleophilic substitution reaction of compund 5b with azido group to obtain compound 9. Thus the azido group of 9 was reduced to amino group in acidic condition in order to protect the amino group formed during reduction reaction and to hydrolize the ester group to carboxylic acid. Subsequent step n) supplies the product 11, e.g. by the deprotection with 48% HBr, the dibromohydrate is obtained. After elution on IRA 402 resin (Cl$^-$) 3,4-diamino butyric acid dichlorohydrate was obtained in a overall yield of 12.3% in six steps starting from 1.

The invention described herein also relates to the direct production of chiral aminocarnitine, phosphonium aminocarnitine and 3,4 diaminobutanoic acid derivatives, that is to say with the advantage of allowing these compounds (of general formula corresponding to intermediate 7a, 7b or 10) to be obtained without first synthesising aminocarnitine or phosphonium aminocarnitine and 3,4 diaminobutanoic acid and then derivatising it, as, in contrast, is envisaged in the above-cited patent applications MI98A001075 and PCT/IT99/00126 for compounds 7a and 7b.

In fact, with the insertion of step a) of the appropriate Y group, after hydrolysis (or catalytic hydrogenation, in the case of an ester removable with that technique) of intermediates 6a or 6b, the desired derivatives of formula 7a or 7b is obtained. Compounds of formula 10 can be obtain by catalytic hydrogenation and hydrolysis of intermediate 9.

Group X can be a leaving group selected, for example, from Br, I, Cl, OX', where X' can be alkyl or aryl sulphonyl (in particular mesyl or tosyl);

The following examples further illustrate the invention. For reference purposes the reader is referred to the reaction scheme on page 9.

EXAMPLE 1

The preparation of (R)-N-tosyl aspartic acid 2 (step a), (R)-N-tosyl aspartic anhydride 3 (step b), and (R)-3-(tosylamino)butano-4-lactone 4 (step c) was done as described in *Helv. Chim. Acta* 1996, 79, 1203–1216 (for 2) and in *Helv. Chim. Acta* 1994, 77, 2142–2146 (for 3 and 4)

Preparation of the Isobutylester of (R)-4-iodo-3-(tosylamino)-butanoic acid 5b (step c')

The solution consisting of 4.1 g (16.06 mmol) of lactone 4.47 ml of anhydrous $CH_2Cl_2$ and 7.4 ml (80.3 mmol) of isobutyl alcohol was cooled to 0° C. in an ice bath and added with 6.55 ml (48.18 mmol) of iodotrimethylsilane. The reaction was left overnight under magnetic stirring at ambient temperature. After this time period water was added and the mixture was left to stir for another 5 minutes at ambient temperature. The organic phase was then washed with $Na_2S_2O_3$ 5%, $H_2O$, dried on $Na_2SO_4$, filtered and evaporated to dryness. The residue thus obtained was purified on a silca gel column, eluting with hexane/ethyl acetate 75:25. 3.07 g of product were obtained as a waxy solid with a yield of 45%;

$^1$H NMR ($CDCl_3$): δ 7.75 (d, 2H), 7.30, (d, 2H), 5.25 (d, 1H) 3.90 (m, 2H), 3.55 (m, 1H), 3.30 (m, 2H), 2.70(dd, 1H), 2.50 (dd, 1H), 2.40 (s, 3H), 1.90 (m, 1H), 1.58 (s, 2H), 0.90 (d, 6H);

ESI Mass=457 [(M+NH$_4$)$^+$];

Elemental analysis for $C_{15}H_{22}NO_4SI$:

Calculated C, 41.01; H, 5.04; N, 3.18;

Found C, 42.15; H, 5.06; N, 3.02.

(As an alternative to chromatography, the crude product was crystallised by ethyl ether/n-hexane to give the product with a yield of 70%).

Preparation of the Isobutylester of (R)-N-tosyl-aminocarnitine iodide 6a (Step f)

1.53 g of iodoester 5b (3.48 mmol) were solubilised in 16 ml of anhydrous chloroform and added with 1.25 ml of 32.7% (6.96 mmol) trimethylamine in iBuOH. The reaction mixture thus obtained was left to react at ambient temperature for 5 days. After this time period the mixture was evaporated to dryness and the white residue was washed by decanting with ethyl ether three times. 1.47 g of product were obtained with a yield of 85%;

MP=173–175° C.;

$[\alpha]^{20}{}_D$=+13.2 (c=0.49 in MeOH);

$^1$H NMR ($CD_3OD$): δ 7.80 (d, 2H), 7.42 (d, 2H), 4.30 (m, 1H), 3.80 (m, 2H), 3.50 (m, 2H), 3.30 (s, 9H), 2.45 (s, 3H), 2.35 (dd, 1H), 2.00 (dd, 1H), 1.80 (m, 1H), 0.90 (d, 6H);

ESI Mass=371 [(M)$^+$];

Ultimate analysis for $C_{18}H_{31}N_2O_4SI$;

Calculated C, 43.37; H, 6.27; N, 5.62;

Found C, 42.89; H, 6.47; N, 5.28,

Alternatively, the reaction was carried out in anhydrous diethylformamide at ambient temperature for 18 hours, precipitating the reaction product with ethyl ether.

Preparation of (R)-N-tosyl-aminocarnitine inner salt 7a (step g)

3.5 g of 6a (7.022 mmol) were solubilised in 28 ml of NaOH 1N (28 mmol) and left overnight to react under magnetic stirring at room temperature. After this period of time, the solution was evaporated to dryness and the 4.8 g residue obtained was purified on a silica gel column, eluting 8.2 with $CHCl_3CH_3OH$. 1.58 g of product were obtained with a yield of 71%;

MP=205–206° C. (dec.);

$[\alpha]^{20}{}_D$=+40.5 (c=0.4 in $H_2O$);

$^1H$ NMR ($CD_3OD$): δ 7.80 (d, 2H), 7.40 (d, 2H), 4.18 (m, 1H), 3.40 (m, 2H), 3.30 (s, 9H), 2.40 (s, 3H), 1.90 (dd, 1H), 1.75 (dd, 1H);

Mass ESI=315 [(M+H)$^+$];

KF=5.8%;

Elemental analysis for $C_{14}H_{22}N_2O_4S$:

Calculated C, 53.48; H, 7.05; N, 8.91;

Calculated with KF: C, 50.39; H, 7.29; N, 8.39;

Found C, 49.39; H, 7.17; N, 8.15,

Preparation of (R)-aminocarnitine inner salt 8a (Starting from 7a, step h)

To the mixture consisting of 530 mg of 7a (1.66 mmol) and 468 mg (4.98 mmol) of phenol were added 6 ml of 48% HBr. The solution obtained was then put in an oil bath preheated to 130° C. and left to reflux for 18 hours. After this time period, the mixture was cooled, diluted with water and extracted twice with ethyl acetate. The aqueous phase was then dried and the oily residue was extracted twice with acetonitrile and evaporated to dryness, until an insoluble solid in acetonitrile was obtained. The solid residue was filtered and dried. 509 mg of (R)-aminocarnitine dibromohydrate were obtained with a yield of 95% ($^1H$ NMR ($D_2O$): δ 4.34 (m, 1H), 3.84 (m, 2H), 3.24 (s, 9H), 3.05 (m, 2H)).

After dissolving in 5 ml of water and elution on IRA 402 (OH$^-$, 9 ml) ion-exchange resin, 252 mg of product were obtained as inner salt (quantitative yield for this latter step); e.e >99% (determined by conversion to the derivative obtained with o-phthalaldehyde and L-acetylcysteine and HPLC analysis, see *J. Chromatography*, 1987, 387, 255–265);

MP=150° C. (decomp);

$[\alpha]^{20}{}_D$=−21.13 (c=0.4 in $H_2O$);

$^1H$ NMR ($D_2O$): δ 3.64 (m, 1H), 3.40 (ddd, 2H), 3.22 (s, 9H), 2.40 (ddd, 2H);

Mass (FAB)=161 [(M+H)$^+$];

Ultimate analysis for $C_7H_{16}N_2O_2$:

calculated C, 52.47; H, 10.06; N, 17.48;

KF=7%;

Calculated with KF: C, 48.79; H, 10.14; N, 16.26;

Found C, 48.77; H, 11.34; N, 16.33.

EXAMPLE 2

Preparation of (R)-aminocarnitine inner salt 8a (Starting from 6a, (Step i))

To the mixture consisting of 827 mg of 6a (prepared according to example 1), (1.66 mmol) and 468 mg (4.98 mmol) of phenol were added 6 ml of HBr 48%. The solution obtained was then placed in an oil bath preheated to 130° C. and left to reflux for 18 hours. Processing and purification were then done as described in the recipe starting from inner salt 7a. The yield was 95%, and the analytical data coincided with those reported above.

EXAMPLE 3

Preparation of (R)-aminocarnitine inner salt 8a (starting from 1, without purification of intermediate products 5b and 6a)

Compound 4, obtained as reported in the references cited above, was reacted with isobutyl alcohol and iodotrimethylsilane, as described in the preparation of 5b. After washing with $Na_2S_2O_3$ 5% and $H_2O$, the organic phase was dried on $Na_2SO_4$, filtered and evaporated to dryness. The residue thus obtained was reacted with trimethylamine as described for obtaining compound 6a, and after evaporation to dryness of the mixture, the residue was hydrolysed as such with HBr, as already described for obtaining compound 8a from 6a. The yield was 38% starting from 1, and the analytical data coincided with those reported above.

EXAMPLE 4

Preparation of the methylester of (R)-4-hydroxy-3-(benzyloxycarbonylamino) butanoic acid 5a (step d)

Compound 4 (2.35 g, 10 mmol) (Y=benzyloxycarbonyl, prepared as described in *J. Am. Chem. Soc.* 1986, 108, 4943–4952) was solubilised in MeOH (15 mL) and added with 18.8 mL (80 mmol) of 25% trimethylamine in MeOH by weight. The reaction was left to stir at room temperature for three days, whereupon $CHCl_3$ was added and the organic phase was washed with HCl 1N and then with NaCl s.s. The organic phase was dried on $Na_2SO_4$, filtered and vacuum evaporated to dryness to yield 2.27 g of an oil containing 90% of product (as shown by NMR analysis) and 10% of starting product;

$^1H$ NMR ($CDCl_3$): δ 7.35 (s, 5H), 5.45 (br, 1H), 5.10 (s, 2H), 4.08 (m, 1H), 3.75 (d, 2H), 3.65 (s, 3H), 2.65 (d, 2H), 1.60 (brs, 1H). This product was used as such in the following reaction.

Preparation of the methylester of (R)-4-mesyloxy-3-(benzyloxycarbonylamino) butanoic acid 5b (step e)

To a solution of 5a (2 g, 7.5 mmol) in anhydrous pyridine (20 mL), cooled to 0° C. in an ice bath, were added 0.87 mL (11.3 mmol) of methane sulphonyl chloride. The solution was then left to stir for one night at room temperature. $CHCl_3$ was added and the organic phase was washed with HCl 1N and then with NaCl s.s. The organic phase was dried on anhydrous $Na_2SO_4$, filtered and vacuum evaporated to dryness to yield 1.96 g of a solid containing approximately 70% product. ($^1H$ NMR ($CDCl_3$): δ 7.35 (s, 5H), 5.45 (br, 1H), 5.20 (s, 2H), 4.33 (brm, 3H), 3.70 (s, 3H), 3.00 (s, 3H), 2.70 (d, 2H)). This product was used as such in the following reaction.

Preparation of the methylester of (R)-N-benzyloxycarbonyl-aminocarnitine methane sulphonate 6a (step f)

To a solution of 5b (527 mg, 1.52 mmol) in 5 mL of anhydrous $CHCl_3$ were added 0.72 mL of a 25% solution by weight of trimethylamine in MeOH, and the solution was left to stir for 5 days at room temperature. A solid containing approximately 65% product was obtained by vacuum evaporation of the solvent ($^1H$ NMR ($CD_3OD$): δ 7.32 (brs, 5H), 5.10 (s, 2H), 4.50 (m 1H), 3.65 (s, 3H), 3.50 (m, 2H), 3.20 (s, 9H), 2.70 (s, 3H), 2.65 (d, 2H).

Preparation of (R)-aminocarnitine inner salt 8a Starting from the Methylester of (R)-N-benzyloxycarbonyl-aminocarnitine methane sulphonate 6a (steps g and h)

The preparation is done by hydrolysing the ester and deprotecting the amine group by means of catalytic hydrogenation according to routine procedures.

EXAMPLE 5

Preparation of (R)-N-decanesulphonyl-aminocarnitine inner salt 7a (steps a–g)

The compound is prepared as described when Y is equal to tosyl, using decansulphonyl chloride instead of tosyl chloride in step a) of the process and then operating as described in the foregoing examples.

EXAMPLE 6

Preparation of (R)-3-tosylamino-4-(trimethylphosphonium)-butanoic acid isobutylester iodide (6b) (step f).

To 2 g of 5b, (4.5 mmol) 5.4 ml of trimethylphosphine (1M solution in THF) were added. The resulting solution was stirred at room temperature for 5 days, then the solvent was removed under vacuum and the residue was triturated three times with diethilic ether to give 1.81 g of 6b (78%);

MP=159–161° C. (decomp);

$[\alpha]_D^{20}$=+21 (c=0.51 in MeOH);

$^1$H NMR (CD$_3$OD): δ 7.75 (d, 2H), 7.40 (d, 2H), 4.10 (m, 1H), 3.70 (d, 2H), 2.60 (m, 2H), 2.40 (s, 3H), 2.30 (m, 1H), 2.10 (m, 1H), 2.00 (d, 9H), 1.80 (m, 1H), 0.82 (d, 6H);

Elemental analysis for $C_{18}H_{31}NO_4PSI$:

Calculated C, 41.95; H, 6.06; N, 2.71; S, 6.22;

Found C, 42.33; H, 6.16; N, 2.88; S, 6.22.

Preparation of (R)-3-tosylamino-4-(trimethylphosphonium)-butanoate (7b) (step g).

1.71 g of 6b (3.3 mmol) were solved in 15.5 ml of NaOH 1N and stirred at room temperature for 20 h, then the aqueous phase was evaporated under vacuum and the crude product was purified by flash chromatography using as eluent a gradient of CHCl$_3$/CH$_3$OH starting from 9/1 to 5/5, to give 530 mg of 7b in 41.4% yield;

MP=192–194° C. (decomp);

$[\alpha]_D^{20}$=+45 (c=0.5 in MeOH);

$^1$H NMR (D$_2$O) δ 7.66 (d, 2H), 7.35 (d, 2H), 3.86 (m, 1H), 2.26–2.50 (m, 5H), 1.72–1.92 (m, 11H);

KF=6.1%;

Elemental analysis for $C_{14}H_{22}NO_4PS$:

Calculated C, 50.74; H, 6.69; N, 4.22, S 9.67;

Calculated with KF: C, 47.66; H, 6.96; N, 3.97; S, 9.08;

Found: C, 47.50; H, 6.85; N, 3.92; S, 8.78.

Preparation of (R)-3-amino-4-(trimethylphosphonium)-butanoate (8b) (step i).

A round bottom flask containing a mixture of 1.9 g of 6b (3.7 mmol), 1.04 g of phenol (11.06 mmol) and 27 ml of HBr 48% was placed in an oil bath previously heated at 130° C. and refluxed for 18 hours. The reaction mixture was then allowed to reach the room temperature, diluted with water and extracted twice with AcOEt. The aqueous layer was evaporated under vacuum, the residue was taken up several times with CH$_3$CN (evaporating under vacuum every time) until a solid residue, insoluble in CH$_3$CN, was obtained. The solid was filtered and then dissolved in 5 mL of water and eluted over an exchange ion resin IRA 402 (OH.) 50 ml. After evaporation under vacuum, the residue was taken up twice with CH$_3$CN and then several times with CH$_3$OH (every time evaporating the solvent under vacuum) to give 600 mg of 8b with a yield of 92%; e.e >99% (determinated as described in ref. 9);

MP=66–68° C. (decomp);

$[\alpha]_D^{20}$=−21.3° (c=1 in H$_2$O);

$^1$H NMR (D$_2$O) δ 3.30 (m, 1H), 2.10–2.35 (m, 4H), 1.75 (d, 9H);

KF=16.3%;

Elemental analysis for $C_7H_{16}NO_2P$:

Calculated C, 47.45; H, 9.10; N, 7.90;

Calculated with KF: C, 39.71; H, 9.44; N, 6.61;

Found: C, 40.30; H, 9.49; N, 6.79.

EXAMPLE 7

Preparation of (R)-3-tosylamino-4-azidobutanoic acid isobutylester (9).

To a solution of 1 g of 5b (2.27 mmol) in 10 ml of CH$_3$CN and 2 ml of water, NaN$_3$ (0.592 g, 9.11 mmol) was added. The resulting suspension was stirred at 80° C. for 6 hours, then the solvent was removed under vacuum and the crude residue was diluted with water and extracted twice with ether. The organic layer was dried over anhydrous Na$_2$SO$_4$, and finally evaporated to obtain 0.790 g of crude product as a light yellow wax which was used without further purification with a yield of 98%;

$[\alpha]_D^{20}$=+15.2° (c=0.45 in MeOH);

$^1$H NMR (CDCl$_3$): δ7.76 (d, 2H), 7.30 (d, 2H), 5.30 (d, 1H), 3.80 (m, 2H), 3.70 (m, 1H), 3.40 (m, 2H), 2.50 (m, 2H), 2.40 (s, 3H), 1.86 (m, 1H), 0.90 (d, 6H);

Elemental analysis for $C_{15}H_{22}N_4O_4S$:

Calculated C, 50.83; H, 6.25; N, 15.80; S 9.04;

Found C, 51.15; H, 6.34; N, 15.41; S, 8.71.

Preparation of (R)-3-tosylamino-4-aminobutyric acid hydrochloride (10).

A solution of 1.1 g of 9 (3.0 mmol) in 143 ml of HCl 2N was hydrogenated in H$_2$ atmosphere overnight at 60 psi. After this time the residue was filtered and the acqueous phase was left under magnetic stirring for additional 48 hours at 40° C. Then the water was evaporated under vacuum and the residue was taken up twice with CH$_3$CN (evaporating under vacuum every time) until a solid residue, insoluble in CH$_3$CN, was obtained. The pale yellow wax was filtered and dried to give 0.300 g of final product with a yield of 32% which was used without further purification;

$[\alpha]_D^{20}$=+43° (c=0.25 in H$_2$O);

$^1$H NMR (D$_2$O): δ 7.70 (d, 2H), 7.35 (d, 2H), 3.75 (m, 1H), 3.00 (m, 2H), 2.10–2.40 (m, 5H).

Preparation of (R)-3,4-diaminobutanoic acid dihydrochloride (11)

A round bottom flask containing a mixture of 0.600 g of 10 (1.94 mmol), 547 mg of phenol (5.82 mmol) and 7.5 ml of HBr 48% was placed in an oil bath previously heated at 130° C. and refluxed for 18 hours. The reaction mixture was then allowed to reach the room temperature, diluted with water and extracted twice with AcOEt. The aqueous layer was evaporated under vacuum, the residue was taken up several times with CH$_3$CN (evaporating under vacuum every time) until a solid residue, insoluble in CH$_3$CN, was obtained. The solid was filtered and dried to give 0.23 g of (R)-3,4-diaminobutanoic acid as dihydrobromide salt (95%) which was solved in 5 ml of water. After elution over 75 ml of exchange ion resin IRA 402 (Cl$^-$) and evaporation under vacuum, the residue was taken up twice with CH$_3$CN and then several times with CH$_3$OH (every time evaporating the solvent under vacuum) to give 0.123 g of 11 as a white wax with a yield of 78%;

$[\alpha]_D^{20} = +4.3°$ (c=1% $H_2O$);

$^1H$ NMR ($D_2O$, DDS): δ 3.85 (m, 1H), 3.35 (m, 2H), 2.75 (dd, 1H), 2.60 (dd, 1H);

KF=21.4%;

Elemental analysis for $C_4H_2N_2O_2Cl_2$:

Calculated C, 25.14; H, 6.33; N, 14.66; Cl, 37.11;

Calculated with KF: C, 19.76; H, 7.37; N, 11.52; Cl, 29.17;

Found: C, 19.49; H, 7.16; N, 11.37; Cl, 38.70.

What is claimed is:

1. Process for the preparation of a compound with the formula:

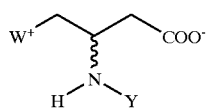

in which

W is $Q(CH_3)_3$ where Q is N or P or

W is $NH_3$

Y is hydrogen or one of the following groups:

—$R_1$,
—$COR_1$,
—$CSR_1$,
—$COOR_1$,
—$CSOR_1$,
—$CONHR_1$,
—$CSNHR_1$,
—$SOR_1$,
—$SO_2R_1$,
—$SONHR_1$,
—$SO_2NHR_1$, where $R_1$ is a straight or branched, saturated or unsaturated alkyl containing from 1 to 20 carbon atoms, optionally substituted with an $A_1$ group, where $A_1$ is selected from the group consisting of halogen, $C_6$–$C_{14}$ aryl or heteroaryl, aryloxy or heteroaryloxy, which can optionally be substituted with straight or branched, saturated or unsaturated lower alkyl or alkoxy, containing from 1 to 20 carbon atoms, halogens; said process comprises the following steps:

a) conversion of D-aspartic or L-aspartic acid to N—Y substituted D-aspartic or L-aspartic acid;

b) conversion of the N—Y substituted D-aspartic or L-aspartic acid to the respective anhydride;

c) reduction of the anhydride obtained in step b) to the corresponding 3-(NH—Y)-lactone;

d) opening of the lactone obtained in step c) to yield the corresponding D-or L-3-(NH—Y)-amino-4-hydroxybutyric acid;

e) transformation of the 4-hydroxy group of the D- or L-3-(NH—Y)-amino-4-hydroxybutyric acid into a leaving group;

f) substitution of the leaving group in position 4 of the D- or L-3-(NH—Y)-aminobutyric acid with a trimethylammonium group, or trimethylphosphonium group;

g) hydrolysis of the ester group; and, if so desired, h) restoration of the amino groups.

2. The process according to claim 1, in which step c is directly followed by step c') consisting in the opening of the lactone to yield the corresponding D- or L-4-X-3-(N—Y)-aminobutyric acid, where X is a leaving group and in which step c') is followed by steps f)–h).

3. The process according to claim 1, in which step f) is followed by step i) consisting in hydrolysis of the ester and deprotection of the 3-amino group to yield R or S aminocarnitine or phosphonium aminocarnitine directly.

4. The process according to claim 1, in which group Y is tosyl.

5. The process according to claim 1 in which the leaving group is iodine.

6. The process according to claim 1, in which the process is conducted without purification of intermediate products.

7. The process of claim 1 including the additional step of one pot hydrolysis of the ester and protective group on N group at position 3.

8. A process for the preparation of a compound with the formula:

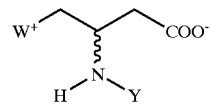

in which

W is $Q(CH_3)_3$ where Q is N or P or

W is $NH_3$

Y is hydrogen or one of the following groups:

—$R_1$,
—$COR_1$,
—$CSR_1$,
—$COOR_1$,
—$CSOR_1$,
—$CONHR_1$,
—$CSNHR_1$,
—$SOR_1$,
—$SO_2R_1$,
—$SONHR_1$,
—$SO_2NHR_1$, where $R_1$ is a straight or branched, saturated or unsaturated alkyl containing from 1 to 20 carbon atoms, optionally substituted with an $A_1$ group, where $A_1$ is selected from the group consisting of halogen, $C_6$–$C_{14}$ aryl or heteroaryl, aryloxy or heteroaryloxy, which can optionally be substituted with straight or branched, saturated or unsaturated lower alkyl or alkoxy, containing from 1 to 20 carbon atoms, halogens;

said process comprises the following steps:

a) conversion of D-aspartic or L-aspartic acid to N—Y substituted D-aspartic or L-aspartic acid;

b) conversion of the N—Y substituted D-aspartic or L-aspartic acid to the respective anhydride;

c) reduction of the anhydride obtained in step b) to the corresponding 3-(NH—Y)-lactone;

d) opening of the lactone obtained in step c) to yield the corresponding D-or L-3-(NH—Y)-amino-4-hydroxybutyric acid;

e) transformation of the 4-hydroxy group of the D- or L-3-(NH—Y)-amino-4-hydroxybutyric acid into a leaving group;

l) substitution of the leaving group in position 4 of the D- or L-3-(NH—Y)-aminobutanoic acid with an azido group;

m) reduction of the azido group to amino group and concurrent hydrolysis of the ester group, and if so desired, n) restoration of the amino group.

9. The process according to claim 8, in which step c is directly followed by step c') consisting in the opening of the lactone to yield the corresponding D- or L-4-X-3-(N—Y)-aminobutyric acid, where X is a leaving group.

10. The process according to claim 8, in which group Y is a tosyl.

11. The process according to claim 8 in which steps l)–n) allow the preparation of a chiral synthon.

12. The process according to claim 11 in which the chiral synthon is R or S 3,4-diaminobutyric acid.

13. The process according claim 8 in which the leaving group is iodine.

14. The process according to claim 8, in which said process is conducted without purification of the intermediate products.

15. A compound of the formula:

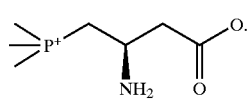

* * * * *